United States Patent
Alford et al.

(10) Patent No.: US 11,241,582 B2
(45) Date of Patent: Feb. 8, 2022

(54) EXTERNALLY POWERED IMPLANTABLE STIMULATOR

(71) Applicant: Medtronic, Inc., Minneapolis, MN (US)

(72) Inventors: Jamu K. Alford, Simi Valley, CA (US); Thaddeus S. Brink, St. Paul, MN (US); Douglas S. Cerny, Minneapolis, MN (US); Sarah J. Offutt, Golden Valley, MN (US); Jerel K. Mueller, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 253 days.

(21) Appl. No.: 15/986,163

(22) Filed: May 22, 2018

(65) Prior Publication Data
US 2019/0358460 A1  Nov. 28, 2019

(51) Int. Cl.
*A61N 1/378* (2006.01)
*A61B 34/20* (2016.01)
(Continued)

(52) U.S. Cl.
CPC .......... *A61N 1/3787* (2013.01); *A61B 5/0031* (2013.01); *A61B 5/01* (2013.01);
(Continued)

(58) Field of Classification Search
CPC .. A61N 1/3601; A61N 1/36071; A61N 1/372; A61N 1/375; A61N 1/3787; A61N 1/378; A61N 1/3782
See application file for complete search history.

(56) References Cited

U.S. PATENT DOCUMENTS 6,208,902 B1  3/2001  Boveja
2007/0156204 A1*  7/2007  Denker ............... A61N 1/3787
                                                    607/61
(Continued)

FOREIGN PATENT DOCUMENTS

CN           1861210        11/2006
WO     2010/059096 A1      5/2010
(Continued)

OTHER PUBLICATIONS

International Search Report and Written Opinion of International Application No. PCT/US2019/025698, dated Jun. 19, 2019, 14 pp.
(Continued)

*Primary Examiner* — Allen Porter
*Assistant Examiner* — Adreanne A. Arnold
(74) *Attorney, Agent, or Firm* — Shumaker & Sieffert, P.A.

(57) ABSTRACT

An example method includes receiving, by an implantable device and from an external device, an energy signal; transducing, by the implantable device, the energy signal into electrical power; outputting, by the implantable device and to the external device, a feedback signal that represents an absolute level of the electrical power transduced from the energy signal, wherein the feedback signal includes a first portion that represents a relative level of the electrical power transduced from the energy signal and a second portion that represents a reference voltage level; and delivering, by the implantable device, a level of electrical stimulation therapy proportional to the absolute level of the electrical power transduced from the energy signal.

38 Claims, 10 Drawing Sheets

(51) Int. Cl.
- *A61B 5/00* (2006.01)
- *A61B 5/01* (2006.01)
- *A61B 5/145* (2006.01)
- *A61N 1/36* (2006.01)
- *A61N 1/372* (2006.01)

(52) U.S. Cl.
CPC ...... *A61B 5/14503* (2013.01); *A61B 5/14532* (2013.01); *A61B 5/14539* (2013.01); *A61B 5/14542* (2013.01); *A61B 5/686* (2013.01); *A61B 5/7228* (2013.01); *A61B 34/20* (2016.02); *A61N 1/36135* (2013.01); *A61N 1/37217* (2013.01); *A61B 2034/2063* (2016.02); *A61B 2562/0247* (2013.01)

(56) References Cited

U.S. PATENT DOCUMENTS

| | | | |
|---|---|---|---|
| 2011/0196452 A1* | 8/2011 | Forsell | H02J 50/10 607/60 |
| 2011/0301668 A1* | 12/2011 | Forsell | A61N 1/3787 607/60 |
| 2012/0119699 A1* | 5/2012 | Carbunaru | H02J 7/0042 320/108 |
| 2013/0193931 A1* | 8/2013 | Bornhoft | H02J 7/0071 320/160 |
| 2014/0163644 A1* | 6/2014 | Scott | A61N 1/3754 607/60 |
| 2014/0336474 A1 | 11/2014 | Arbabian et al. | |
| 2015/0249344 A1* | 9/2015 | Poon | H02J 50/402 307/23 |
| 2017/0201131 A1 | 7/2017 | Vihvelin et al. | |
| 2021/0101007 A1 | 4/2021 | Hamner et al. | |
| 2021/0205619 A1 | 7/2021 | Wong et al. | |

FOREIGN PATENT DOCUMENTS

| | | |
|---|---|---|
| WO | 2014/089392 A1 | 6/2014 |
| WO | 2017132067 A2 | 8/2017 |
| WO | 2019143790 A1 | 7/2019 |

OTHER PUBLICATIONS

Bocan et al., "Adaptive Transcutaneous Power Transfer to Implantable Devices: A State of the Art Review" Sensors, Mar. 2016, 23 pp.

Wang, et al., "Closed-Loop Ultrasonic Power and Communication with Multiple Minaturized Active Implantable Medical Devices," 2017 IEEE International Ultrasonics Symposium (IUS), Sep. 2017, 4 pp.

Charthad, et al., "A mm-Sized Implantable Medical Device (IMD) with Ultrasonic Power Transfer and a Hybrid Bi-Directional Data Link," IEEE Journal of Solid-State Circuits, vol. 50, No. 8, Aug. 2015, pp. 1741-1753.

Shmilovitz, et al., "Noninvasive Control of the Power Transferred to an Implanted Device by an Ultrasonic Transcutaneous Energy Transfer Link," IEEE Transactions on Biomedical Engineering, vol. 61, No. 4, Apr. 2014, pp. 995-1004.

* cited by examiner

EXTERNALLY POWERED IMPLANTABLE STIMULATOR

TECHNICAL FIELD

This disclosure generally relates to medical devices and, more particularly, to systems for electrical stimulation of a patient.

BACKGROUND

Medical devices, including implantable medical devices (IMDs), may be used to treat a variety of medical conditions. Medical electrical stimulation devices, for example, may deliver electrical stimulation therapy to a patient via external and/or implanted electrodes. Electrical stimulation therapy may include stimulation of nerve tissue, muscle tissue, the brain, the heart, or other tissue within a patient. In some examples, an electrical stimulation device is fully implanted within the patient. For instance, an implantable electrical stimulation device may include a power source, an implantable electrical stimulation generator, and one or more implantable electrodes. In some examples, an electrical stimulation system may include some components implantable within the patient and some components external to the patient.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via electrodes implantable proximate to the spinal cord, gastrointestinal organs, tibial nerve, sacral nerve, peripheral nerves, or within the brain of a patient.

SUMMARY

In one example, a method includes wirelessly outputting, by an external device, an energy signal to be transduced into electrical power by an implantable device that delivers a level of electrical stimulation therapy proportional to a level of the electrical power transduced from the energy signal; wirelessly receiving, by the external device and from the implantable device, a feedback signal having a first portion that represents a relative level of the electrical power transduced from the energy signal and a second portion that represents a reference voltage level; determining, by the external device and based on the first portion and the second portion of the feedback signal, an absolute level of the electrical power transduced from the energy signal; adjusting, by the external device and based on the determined absolute level of the electrical power, a level of the energy signal to control the level of electrical stimulation therapy delivered by the implantable device; and outputting, by the external device, the energy signal with the adjusted level.

In another example, an external device includes a transmitter configured to wirelessly output an energy signal to be transduced into electrical power by an implantable device that delivers a level of electrical stimulation therapy proportional to a level of the electrical power transduced from the energy signal; a receiver configured to wirelessly receive, from the implantable device, a feedback signal having a first portion that represents a relative level of the electrical power transduced from the energy signal and a second portion that represents a reference voltage level; and one or more processors configured to: determine, based on the first portion and the second portion of the feedback signal, an absolute level of the electrical power transduced from the energy signal; adjust, based on the determined absolute level of the electrical power, a level of the energy signal to control the level of electrical stimulation therapy delivered by the implantable device; and cause the transmitter to output the energy signal with the adjusted level.

In another example, a method includes wirelessly receiving, by an implantable device and from an external device, an energy signal; transducing, by the implantable device, the energy signal into an electrical signal; generating, from the electrical signal, a feedback signal that includes a first portion that represents a variable feedback input and a second portion that represents a reference voltage level; wirelessly outputting, by the implantable device and to the external device, the feedback signal; and delivering, by the implantable device, a level of electrical stimulation therapy proportional to an absolute level of the electrical power transduced from the energy signal.

In another example, an implantable device includes a receiver configured to wirelessly receive, from an external device, an energy signal; a transducer configured to convert the energy signal into an electrical signal; a feedback signal generator configured to generate, from the electrical signal, a feedback signal that includes a first portion that represents a variable feedback input a second portion that represents a reference voltage level; a transmitter configured to output, to the external device, the feedback signal; and circuitry and one or more electrodes collectively configured to deliver electrical stimulation therapy with an amplitude that is proportional to an absolute level of the electrical power transduced from the energy signal.

In another example, a system includes an external device configured to output an energy signal; an implantable device configured to: measure a condition of a patient in which the implantable device is implanted; transduce the energy signal into electrical power; output a feedback signal that represents an absolute level of the electrical power transduced from the energy signal, wherein the feedback signal includes: a first portion having a first parameter that represents a relative level of the electrical power transduced from the energy signal and a second parameter that represents a value of the measured condition, and a second portion that represents a reference voltage level; and deliver a level of electrical stimulation therapy proportional to the absolute level of the electrical power transduced from the energy signal, wherein the external device is further configured to: determine, based on the second parameter of the first portion of the feedback signal, the value of the measured condition; determine, based on the first portion and the second portion of the feedback signal, an absolute level of the electrical power transduced from the energy signal; adjust, based on the determined absolute level of the electrical power, a level of the energy signal; and output the energy signal with the adjusted level.

In another example, a method includes receiving, by an implantable device and from an external device, an energy signal, wherein the implantable device does not include a stimulation generator or a battery; transducing, by the implantable device, the energy signal into an electrical signal; measuring, by a sensor of the implantable device, a condition of a patient in which the implantable device is implanted; generating, from the electrical signal, a feedback signal by setting an amplitude of a portion of the electrical signal according to a level of the measured condition; outputting, by the implantable device and to the external device, the feedback signal; and delivering, by the implantable device, a level of electrical stimulation therapy proportional to an absolute level of the electrical power transduced from the energy signal.

In another example, a method includes outputting, by an external device, an energy signal to be transduced into electrical power by an implantable device that delivers a level of electrical stimulation therapy proportional to a level of the electrical power transduced from the energy signal, wherein the implantable device does not include a stimulation generator or a battery; receiving, by the external device and from the implantable device, a feedback signal that includes a truncation point that represents a level of a condition of a patient in which the implantable device is implanted, wherein the level of the condition is measured by a sensor included in the implantable device; and determining, by the external device and based on the feedback signal, the level of the measured condition.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
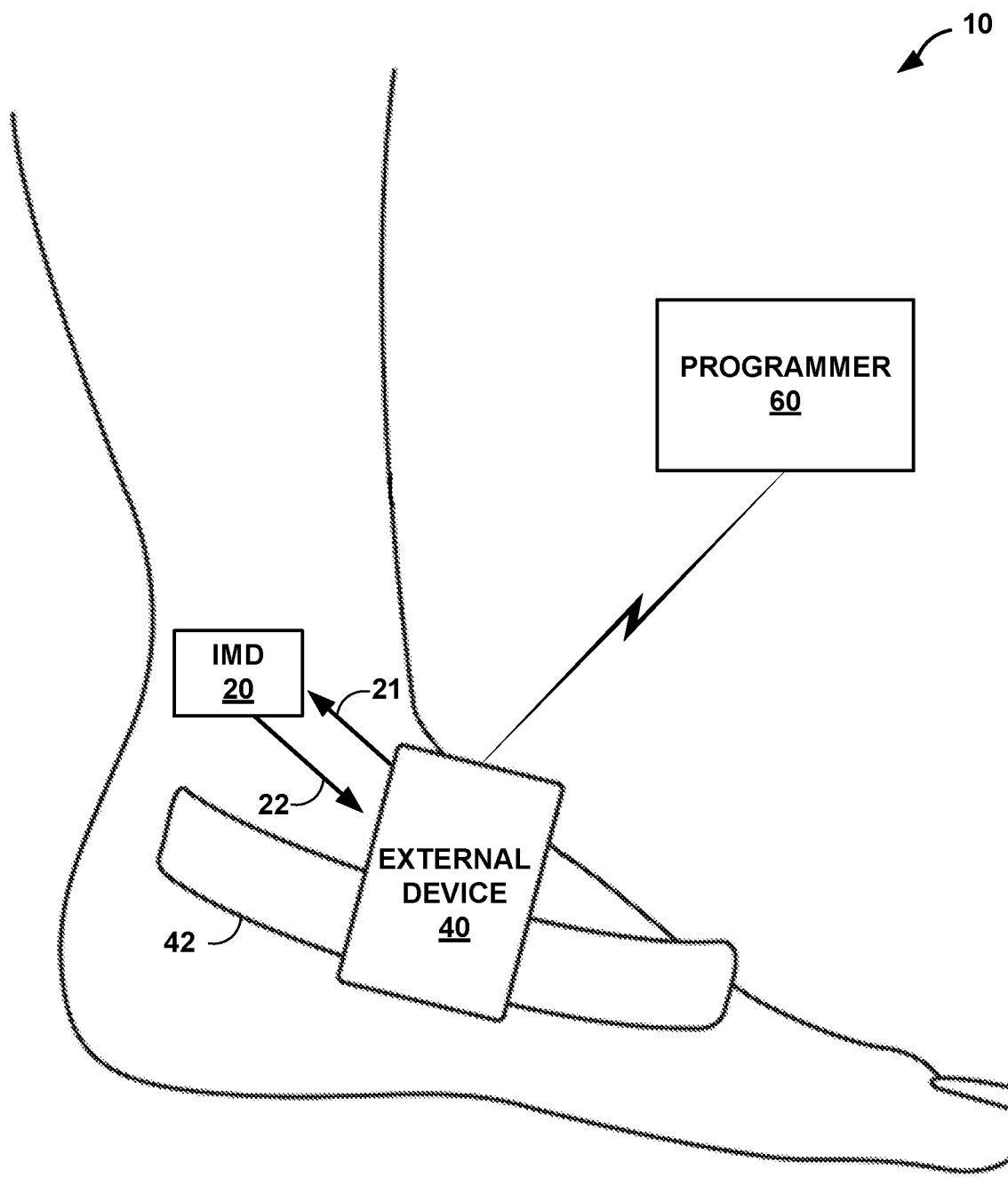
FIG. 1 is a schematic diagram of a minimally invasive INS system 10 capable of delivering a neurostimulation therapy, in accordance with one or more techniques of this disclosure.

In general, this disclosure describes devices, systems, and techniques for controlling an amount of therapy delivered by an implantable device. An external device may output energy signals to wirelessly transmit power to the implantable device. The implantable device may transduce the energy signal into electrical power that the implantable device uses to deliver therapy (e.g., electrical stimulation).

In some examples, it may be desirable for the implantable device to be as small as possible. As such, it may be desirable to minimize an amount and/or a size of components included in the implantable device. One way to accomplish this goal is to make the implantable device "dumb" in that the implantable device may simply deliver an amount of therapy (e.g., a level of electrical stimulation) proportional to a level of the electrical power transduced from the energy signal generated by the external device. By delivering an amount of therapy proportional to the level of the transduced electrical power, the implantable device may not require, and may omit, various components used to intelligently deliver therapy. Instead, these components may be included in the external device, for which size is less of a concern.

The wireless transmission of power may require choosing a specific location 3-dimensionally at which the external device focuses multiple energy signals. An example of an external energy signal is an ultrasound signal. The multiple energy signals focused at the specific location may be phase-shifted ultrasound signals. As the patient moves, the location of the implantable device in relation to the external device may change. Additionally, in order to deliver sufficient energy, the energy signals may need to be focused to a very small focal point. With a small focal point, it is easy for the focal point to not be aimed properly and for the signals to miss the intended target altogether or partially, in which case transfer efficiency of the energy signal will be degraded.

However, the implantable device may not have its own source of power and may simply deliver a level of therapy proportional to the received power. As such, to ensure that the implantable device is properly targeted and to control the amount of therapy delivered, it may be desirable for the external device to be able to determine how much power is being received by the implantable device.

In some examples, the external device may determine how much power is being received by the implantable device based on a feedback signal generated by the implantable device and transmitted to the external device. For instance, the implantable device may transduce the received energy signal(s) into electrical power and output a feedback signal that indicates a level of the electrical power transduced. However, if the implantable device merely outputs a feedback signal with a level corresponding to the level of the electrical power transduced, the external device may not be able to determine the absolute level of the electrical power because the scale of the feedback signal as received by the external device may vary based on distance.

In accordance with techniques of this disclosure, the implantable device may output a feedback signal that represents an absolute level of the electrical power transduced by the implantable device from the energy signal. The implantable device may output the feedback signal with a first signal portion that represents a relative voltage level of the electrical power transduced from the energy signal and a second signal portion that represents a reference voltage level (e.g., a calibrated voltage level). For instance, the implantable device may include a calibrated diode placed parallel across a transmit antenna for the feedback signal. Forward current would provide the first signal portion and reverse current would be capped at the diode forward voltage, providing the second, reference, signal portion.

The external device may determine the absolute level of the electrical power at the IMD. transduced by the implantable device based on the first and second portions of the feedback signal. As used herein, the term absolute refers to an actual value as opposed to either a relative value (e.g., relative value caused by coupling losses between the IMD and external device) or an absolute value in the unsigned mathematical sense. For instance, the external device may determine an absolute voltage amplitude of the transduced electrical power based on an amplitude of one or more peaks in the feedback signal (e.g., one or more peaks in the first signal portion) in comparison to one or more truncation points in the feedback signal (e.g., one or more truncation points in the second signal portion).

Based on the determined absolute level, the external device may adjust a level of the energy signals transmitted to the implantable device. For example, the external device may increase and/or decrease the level (e.g., duration and/or intensity) of the energy signal based on the feedback signal to maintain the level of transduced electrical power in a desired range, above a desired threshold level and/or below a desired threshold level. In this way, as the implantable device delivers a level of therapy proportional to a level of the electrical power transduced from the energy signal, the external device may establish closed-loop control over the level of therapy delivered to the patient.

The techniques of this disclosure may also be used to locate, and determine a position of, the implantable device. For instance, the external device may search a volume of space by sweeping a target of the energy signals. While sweeping the target, the external device may maintain a particular level of the energy signals. For each target location, the external device may receive a feedback signal and determine an absolute amount of power transduced by the implantable device. The external device may identify the target location that results in the greatest absolute amount of power as the location of the implantable device.

Once the location of the implantable device is determined, the external device may output energy signals to the determined location. In this manner, the external device may promote better coupling of the energy signal to the target and, hence, more effective transfer of energy to the implantable device. In some examples, the external device may repeat the location searching, either continuously or intermittently, and update the determined location.

FIG. 1 is a schematic diagram of a minimally invasive INS system 10 capable of delivering a neurostimulation therapy, in accordance with one or more techniques of this disclosure. Example system 10 includes an implantable medical device (IMD) 20, an external device 40, and a programming device 60.

IMD 20 includes electronic circuitry, e.g., comprising one or more electronic circuits, for delivering electrical stimulation therapy enclosed in a sealed housing and coupled to therapy delivery electrodes. IMD 20 may be configured to receive energy signals and transduce the received energy signals into electrical power that is used to deliver the electrical stimulation therapy. For instance, IMD 20 may collect (e.g., harvest) energy signals 21 and transduce the collected energy signals 21 into electrical power.

IMD 20 may be configured to deliver an amount of electrical stimulation in proportion to a level of the electrical power transduced. For instance, as opposed to including a power source and processing circuitry that determines when and how to deliver electrical stimulation, IMD 20 may deliver electrical stimulation directly in response to and based on energy signals 21. As such, changes in the amplitude, pulse width, or pulse rate of energy signals 21 may result in an adjustment of an amplitude, pulse width, or pulse rate of the therapy delivered by IMD 20.

In some examples, IMD 20 is less than approximately 30 mm in length, less than approximately 2 mm in diameter, and less than approximately 1 cc in volume. In illustrative examples, the term "approximately" as used herein may indicate a value of +10% of a stated value or may correspond to a range of manufacturing specification tolerances. In other examples, IMD 20 may be less than approximately 3 mm in length, less than approximately 15 mm in diameter, and less than approximately 0.6 cc in volume. IMD 20 may be approximately 0.1 cc in volume in some examples. The examples described herein are not limited to a particular size and volume of IMD 20 but are generally implemented to enable the use of a reduced size device for minimally invasive implantation procedures (e.g., injection) and minimized discomfort to a patient. It is recognized, however, that the various IMD systems described herein may be implemented in conjunction with a wide variety of IMD sizes and volumes adapted for a particular therapy application.

External device 40 may be a wearable device including a strap 42 or other attachment member(s) (e.g., adhesive) for securing external device 40 to the patient in operable proximity to IMD 20. In some examples, external device 40 may be a patch worn by the patient. External device 40 may be a power transmission device that is worn by the patient during a therapy session to provide power that results in the delivery of electrical stimulation. For example, external device 40 may output energy signals 21 for receipt by IMD 20. As discussed above, the receipt of energy signals 21 by IMD 20 may result in the delivery of electrical stimulation by IMD 20. Examples of energy signals 21 include, but are not limited to mechanical energy (e.g., ultrasound waves that may be in the range of 500 kHz to 1 MHz, or in the range of 100 kHz to 5 MHz), optical energy, electromagnetic energy, or any other energy signal type capable of transcutaneously providing power to an implantable medical device.

External device 40 may be a battery powered device including a transmitter used to transcutaneously transmit energy signals 21 to a receiver included in IMD 20. External device 40 may include one or more primary and/or rechargeable cells and therefore may include a power adaptor and plug for re-charging in a standard 110V or 220V wall outlet, for example.

External device 40 may be configured to control the amount of therapy delivered by IMD 20. In some examples, external device 40 may adjust various parameters of energy signals 21 in order to adjust corresponding parameters of electrical stimulation therapy delivered by IMD 20. For instance, as discussed below with reference to FIG. 2, external device 40 may adjust an amplitude of energy signals 21 to adjust an amplitude of the electrical stimulation delivered to the patient by IMD 20. Similarly, external device 40 may adjust a pulse width of energy signals 21 to adjust a pulse width of the electrical stimulation delivered to the patient by IMD 20 and/or a pulse rate of energy signals 21 to adjust a pulse rate of the electrical stimulation delivered to the patient by IMD 20.

In order to wirelessly transmit power to IMD 20, external device 40 may select a specific location 3-dimensionally at which to focus energy signals 21 (e.g., phase-shifted ultrasound signals). Ideally, the selected location will correspond to a location of IMD 20. However, as the patient moves, the location of IMD 20 in relation to external device 40 may change. Additionally, in order to deliver sufficient energy, energy signals 21 may need to be focused to a very small focal point. With a small focal point, it is easy for the focal point to not be aimed properly and for the signals to miss the intended target partially or altogether. As such, to ensure that IMD 20 is properly targeted and to control the amount of therapy delivered, it may be desirable for external device 40 to be able to determine how much power is being received by IMD 20.

In accordance with techniques of this disclosure, IMD 20 may output a feedback signal 22 that represents an absolute level of the electrical power transduced from energy signals 21. IMD 20 may output feedback signal 22 with a first signal portion that represents a relative voltage level of the electrical power transduced from energy signals 21 and a second signal portion that represents a reference voltage level (e.g., a calibrated voltage level) that is known to external device 40 (e.g., external device 40 may include memory that is pre-programmed with the reference voltage level). For instance, IMD 20 may include a calibrated diode parallel across a transmit antenna for feedback signal 22. Forward current would provide the first signal portion and reverse current would be capped at the diode forward voltage, providing the second signal portion. Examples of feedback signal 22 include, but are not limited to, radiofrequency (RF) signals, ultrasound echo signals, infrared or other optical signals, or any other signal capable of transcutaneous propagation.

External device 40 may determine the absolute level of the electrical power transduced by IMD 20 based on the portions of feedback signal 22. For instance, external device 40 may determine an absolute voltage amplitude of the transduced electrical power based on an amplitude of one or more peaks in feedback signal 22 (where the peaks are part of the first signal portion) in comparison to one or more truncation points in feedback signal 22 (where the truncation points are part of the second signal portion).

Based on the determined absolute level, external device 40 may adjust one or more parameters of energy signals 21. For instance, if the determined absolute level indicates that IMD 20 is not receiving enough power, external device 40 may increase an amplitude of energy signals 21. In this way, external device 40 may establish closed-loop control over the level of therapy delivered to the patient by IMD 20.

Programmer 60 may be configured to program external device 40 for operation to cause delivery of therapy to the patient. For example, programmer 60 may be configured to program one or more of the following parameters of external device 40: pulse amplitude, pulse width, pulse shape, pulse frequency, duty cycle, and therapy on and off times. External device 40 may use the parameters to generate energy signals that will cause an implantable device (e.g., IMD 20) to deliver stimulation with the desired attributes (e.g., pulse amplitude, pulse width, pulse shape, pulse frequency, duty cycle, and therapy on and off times). In some examples, programmer 60 may be a clinician programmer that may be able to program all of the parameters of external device 40. In some examples, programmer 60 may be a patient programmer that may be able to program a subset of the parameters of external device 40.

Programmer 60 may be configured to communicate directly with external device 40 via any suitable wired or wireless link. Programmer 60, for example, may communicate via wireless communication with external device 40 using radio frequency (RF) telemetry techniques known in the art or other communication standards such as, for example, Bluetooth®. Programmer 60 may also communicate with another programmer or computing device via a wired or wireless connection using any of a variety of local wireless communication techniques, such as RF communication according to the 802.11 or Bluetooth® specification sets, infrared communication according to the IRDA specification set, or other standard or proprietary telemetry protocols. Programmer 60 may also communicate with another programming or computing device via exchange of removable media, such as magnetic or optical disks, or memory cards or sticks. Further, programmer 60 may communicate with external device 40 and other programming devices via remote telemetry techniques known in the art, communicating via a local area network (LAN), wide area network (WAN), public switched telephone network (PSTN), or cellular telephone network, for example.

It is contemplated that in some examples the functionality required for transmitting power to IMD 20 and for controlling therapy delivery may be implemented in a single external device. For example, power transmission capability of external device 40 and programming capabilities of programmer 60 may be combined in a single external device, which may be a wearable or handheld device.

While IMD 20 is shown in FIG. 1 as being implanted along a portion of the lower leg of the patient, IMD 20 could be implanted at numerous sites according to patient need and the particular medical application. In the illustrative embodiment, IMD 20 is provided for stimulating the tibial nerve of the patient to treat overactive bladder syndrome and is merely one example of the type of medical application for which INS system 10 may be used. In another example, IMD 20 may be implanted to deliver a stimulation therapy to muscles of the pelvic floor, such as periurethral muscles or the external urethral sphincter for treating symptoms of urinary incontinence or overactive bladder syndrome. In other examples, IMD 20 may be deployed for delivering neurostimulation therapy to an acupuncture point for treatment of a symptom associated with the acupuncture point. IMD 20 may be implemented in an INS system for providing numerous types of neurostimulation therapies, such as for pain control, autonomic nervous system modulation, functional electrical stimulation, tremor, and more.

As shown in FIG. 1, IMD 20 may, in some examples, be provided for tibial stimulation. For instance, external device 40 may cause IMD 20 to deliver appropriate stimulation for tibial stimulation to alleviate urinary incontinence. External device 40 may be worn full-time, part-time, or intermittently. For instance, when used for tibial stimulation, external device 40 may be worn intermittently because tibial stimulation may provide a lingering carryover effect, such that stimulation may be delivered once every one to seven days and its effect will last until the next stimulation session.

Figure 2:
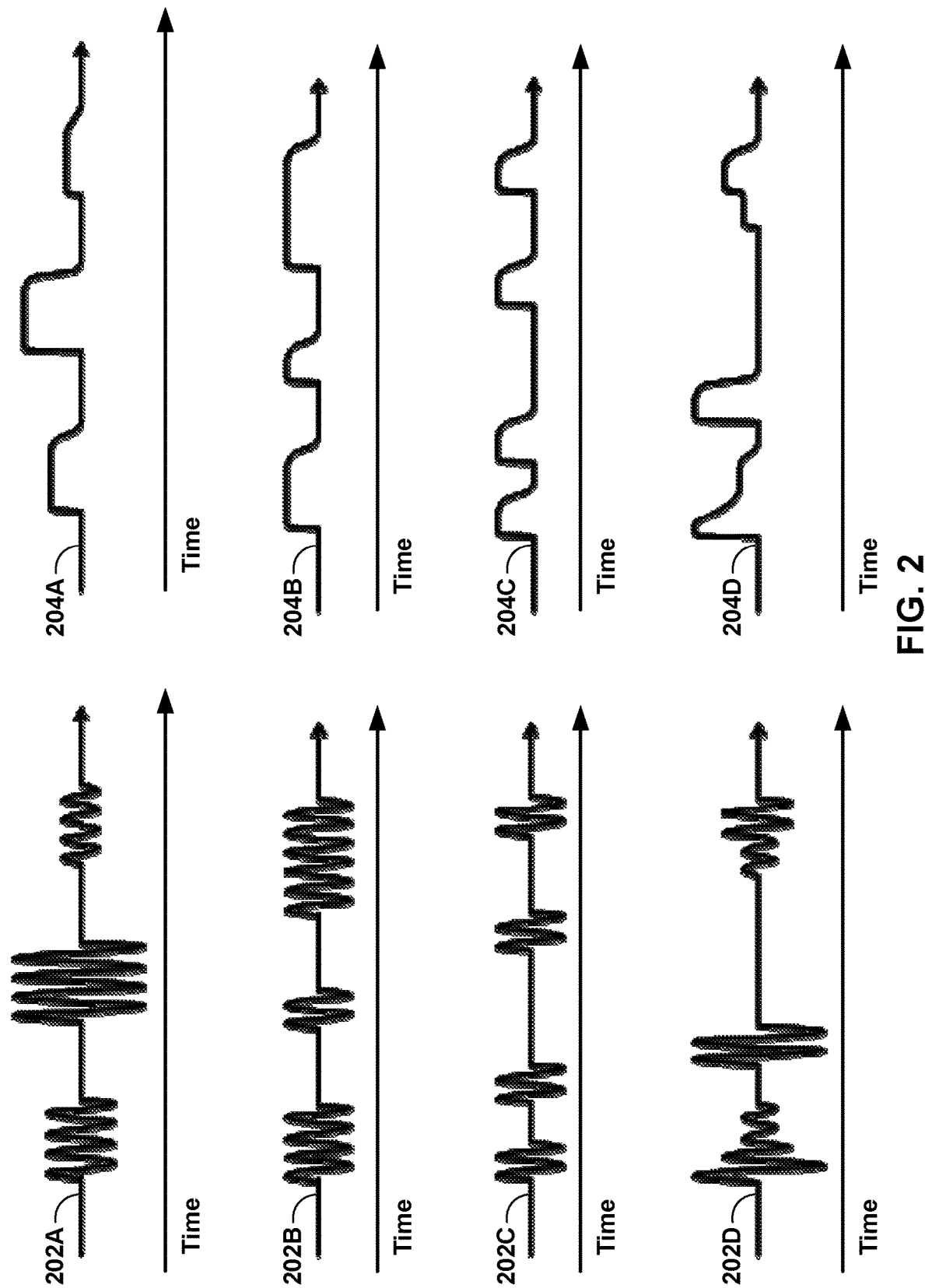
FIG. 2 is a set of graphs illustrating energy signals and resulting electrical stimulation therapy, in accordance with one or more techniques of this disclosure.

FIG. 2 is a set of graphs illustrating energy signals and resulting electrical stimulation therapy, in accordance with one or more techniques of this disclosure. Each of graphs 202A-202D (collectively "graphs 202") illustrate an energy signal that may be received by an implantable medical device. Each of graphs 204A-204D (collectively "graphs 204") illustrate electrical stimulation therapy that may be delivered by an implantable medical device. For instance, each of graphs 202 may illustrate an example of an energy signal 21 (e.g., an ultrasound signal) that may be received by IMD 20 of FIG. 1 and each of graphs 204 may illustrate a corresponding electrical stimulation therapy that may be delivered by IMD 20 of FIG. 1. In particular, IMD 20 may deliver the electrical stimulation therapy of graph 204A in response to receiving the energy signal of graph 202A, IMD 20 may deliver the electrical stimulation therapy of graph 204B in response to receiving the energy signal of graph 202B, IMD 20 may deliver the electrical stimulation therapy of graph 204C in response to receiving the energy signal of graph 202C, and IMD 20 may deliver the electrical stimulation therapy of graph 204D in response to receiving the energy signal of graph 202D.

As can be seen from graph 202A and graph 204A, the amplitude of the electrical stimulation is proportional to the amplitude of the energy signal (i.e., proportional, or having a similar shape, to the mechanical amplitude of the ultrasound signal). As can be seen from graph 202B and graph 204B, in this example, the pulse width of the electrical stimulation is proportional to the pulse width of the energy signal. In some example, such as the example of graphs 202B and 204B where the energy signal is an oscillatory signal, the pulse width of the energy signal may be interpreted as the width of a group of pulses as opposed to the width of an individual pulse (e.g., graph 202B includes a first group of four pulses, a second group of two pulses, and a third group of six pulses that result in the generation of a first pulse four units wide, a second pulse two units wide, and a third pulse six units wide). As can be seen from graph 202C and graph 204C, the pulse rate of the electrical stimulation is proportional to the pulse rate of the energy signal. Finally, as can be seen from graph 202D and graph 204D, the amplitude, pulse width, and pulse rate of the energy signal may all simultaneously be adjusted to adjust the amplitude, pulse width, and pulse rate of the electrical stimulation.

Figure 3:
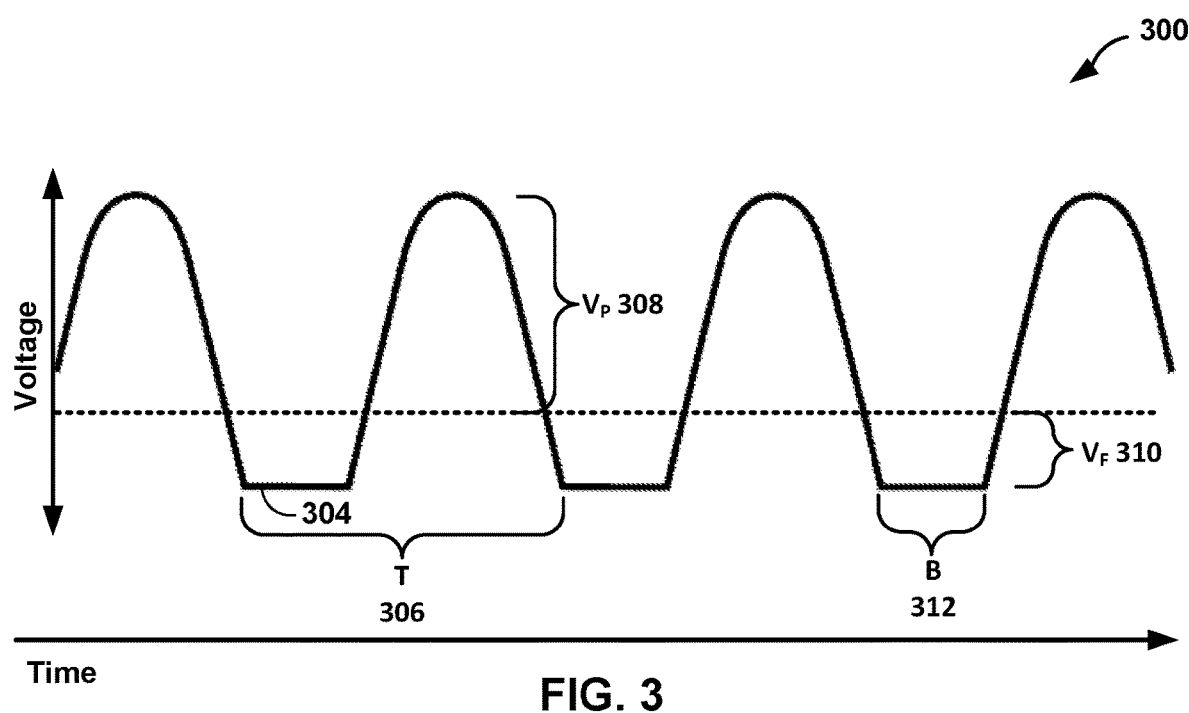
FIG. 3 is a graph illustrating an example feedback signal generated by an implantable medical device, in accordance with one or more techniques of this disclosure.

FIG. 3 is a graph illustrating an example feedback signal generated by an implantable medical device, in accordance with one or more techniques of this disclosure. Graph 300 may represent a feedback signal generated by an implantable medical device. For instance, graph 300 may represent feedback signal 22 generated by IMD 20 and received by external device 40 of FIG. 1. As can be seen from FIG. 3, the feedback signal may be periodic and may include truncation points (e.g., truncation point 304).

As discussed above, an implantable medical device, such as IMD 20, may generate a feedback signal that includes a first signal portion that represents a relative voltage level of the electrical power transduced from an energy signal by the IMD and a second signal portion that represents a reference voltage level. In the example of FIG. 3, the untruncated portions of the feedback signal may be considered to be the first signal portion of the feedback signal and the truncated portions may be considered to be the second signal portion of the feedback signal. The feedback signal may be an electrical signal that is wirelessly transmitted by IMD 20 to external device 40, e.g., by an antenna of IMD 20.

Various aspects of the feedback signal are marked on FIG. 3. In particular, the period of the feedback signal is marked as T 306, the peak voltage of the first signal portion is marked as $V_P$ 308, the reference voltage of the second signal portion (e.g., the forward voltage of a diode) is marked as $V_F$ 310, and the time duration of the truncation (e.g., diode clipping) is marked as B 312.

Figure 4:
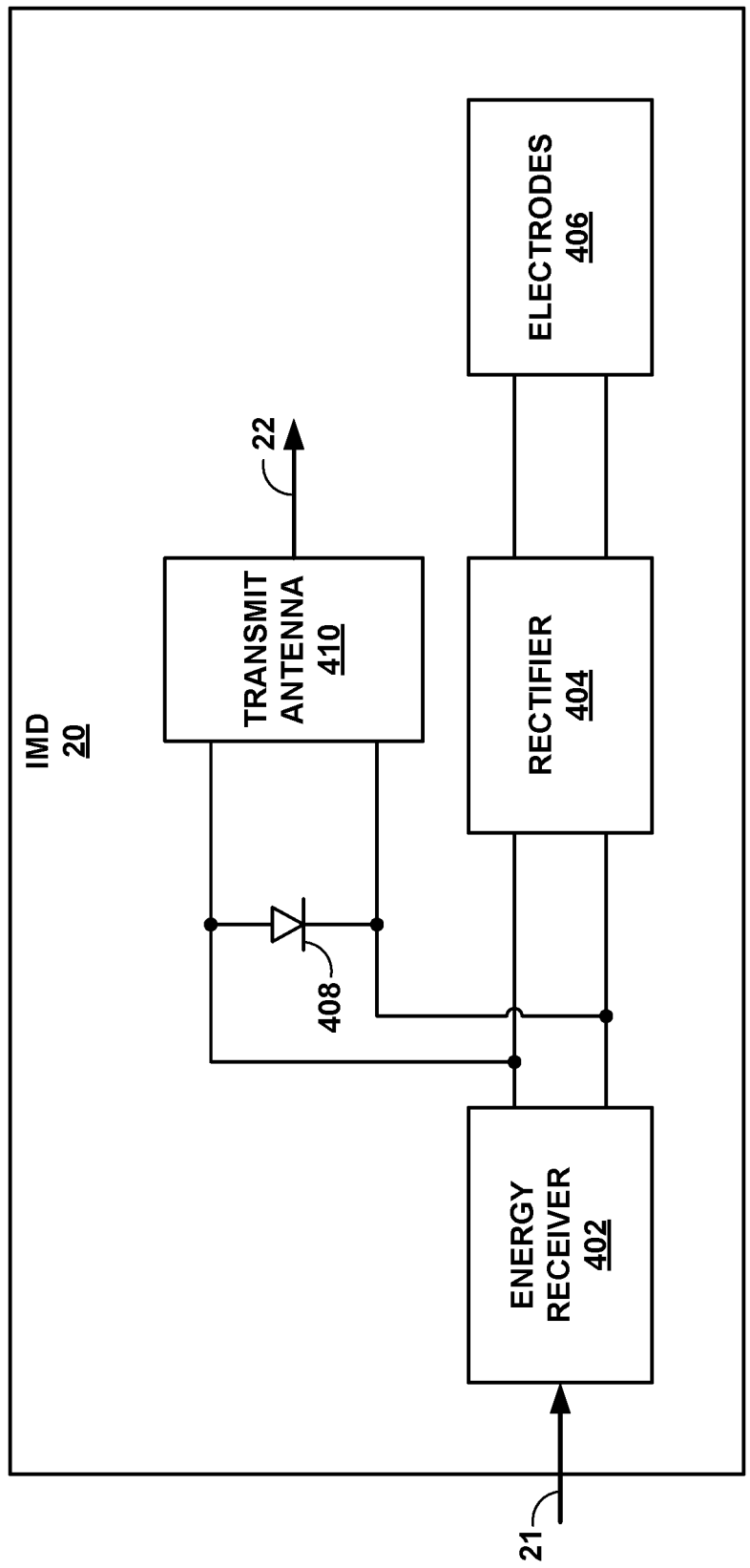
FIG. 4 is a block diagram illustrating further details of one example of an implantable medical device, in accordance with one or more techniques of this disclosure.

FIG. 4 is a block diagram illustrating further details of one example of an implantable medical device, in accordance with one or more techniques of this disclosure. As illustrated in FIG. 4, IMD 20 may include an energy receiver 402, a rectifier 404, one or more electrodes 406, a diode 408, and a transmit antenna 410.

Energy receiver 402 may be configured to collect, harvest, or otherwise receive energy signals and transduce or otherwise convert the received energy signals into electrical power. For instance, energy receiver 402 may transduce energy signals 21 into electrical power. Where energy signals 21 include periodic signals, such as periodic ultrasound waves, energy receiver 402 may transduce energy signals 21 into AC electrical power. In some examples, energy receiver 402 may include piezoelectric material that harvests an ultrasound signal and converts it into an electrical signal. In some examples, energy receiver 402 may include a coil that harvests an electromagnetic signal and converts it into an electrical signal.

Rectifier 404 may be configured to convert transduced electrical power. For instance, rectifier 404 may convert AC electrical power output by energy receiver 402 (e.g., electrical power transduced from ultrasound signals) into DC electrical power. As one example, rectifier 404 may be formed from a plurality of diodes in a full or half-bridge configuration. In some examples, IMD 20 may include additional circuitry, such as impedance matching or signal conditioning circuitry. The additional circuitry may be located either before rectifier 404, after rectifier 404, or both before and after rectifier 404. The additional circuitry, rectifier 404, and electrodes 406 may be collectively configured to deliver a level of electrical stimulation therapy proportional to the absolute level of the electrical power transduced from the energy signal. In particular, IMD 20 may not include any stimulation generator that intelligently generates stimulation waveforms based on a therapy program (e.g., IMD 20 may not include a stimulation generator similar to stimulation generator 806 of external device 40 of FIG. 8).

Electrodes 406 may be configured to deliver electrical stimulation to a patient. For instance, electrodes 406 may conduct electrical signals from rectifier 404 into a tissue of the patient. Electrodes 406 may be located on a housing of IMD 20, on one or more leads connected to the housing of IMD 20, or a combination. Electrodes 406 may be any suitable type of electrode. Examples of electrodes 406 include, but are not limited to, pad electrodes, ring electrodes, paddle electrodes, or any other type of electrode capable of delivering electrical stimulation to a patient.

In some examples, IMD 20 may include multiple receiver/rectifier/transmit pathways within the housing to allow multiple channels of stimulation through different sets of electrodes. In such examples, external device 40 may target different energy receivers to control delivery of therapy by various electrodes. For instance, external device 40 may target an energy receiver 402 of a first pathway to cause electrodes of the first pathway to deliver therapy and/or target an energy receiver 402 of a second pathway to cause electrodes of the second pathway to deliver therapy. In some examples, IMD 20 may include additional circuitry before transmit antenna 410 (e.g., together with diode 408) to allow a unique feedback signal 22 from each receiver/rectifier/transmit pathway. In this manner, external device 40 may discern between the various receiver/rectifier/transmit pathways and corresponding electrodes. Additionally, multiple receiver/rectifier/transmit pathways may be connected in parallel with electrodes 406 to allow flexibility in the targeting of energy signals 21 by external device 40. Such an implementation may also have additional circuitry before transmit antenna 410 to discern between the various receiver/rectifier/transmit pathways and corresponding electrodes.

As discussed above and in accordance with one or more techniques of this disclosure, IMD 20 may generate a feedback signal that represents an absolute level of the electrical power transduced from the energy signal. For example, IMD 20 may output feedback signal 22 that a first signal portion that represents a relative voltage level of the electrical power transduced from the energy signal and a second signal portion that represents a reference voltage level (e.g., a calibrated voltage level). In this sense, the relative voltage level may convey a shape of the transduced electrical power but may not convey an absolute level of the transduced electrical power (e.g., a shape but not a gain).

IMD 20 may include one or more components configured to generate and transmit the feedback signal. As shown in the example of FIG. 4, IMD 20 may include diode 408 and transmit antenna 410 that are collectively configured to generate and wirelessly transmit feedback signal 22. As discussed above, energy receiver 402 may transduce energy signals 21 into AC electrical power. For instance, energy receiver 402 may transduce energy signals 21 into AC electrical power having a waveform shown by the non-truncated regions of FIG. 3. Diode 408 may receive the AC electrical power and introduce truncated regions (e.g., truncated regions 304 of FIG. 3). For instance, diode 408 may be connected parallel with respect to transmit antenna 410 such that the reverse current is capped at a forward voltage of diode 408. Similarly, diode 408 may be positioned in series with energy receiver 402 to achieve a similar result (e.g., the truncation of portions of the AC electrical power signal generated by energy receiver 402). In some examples, diode 408 may include a single diode. In some examples, diode 408 may include multiple diodes and the reference voltage may be the voltage across all of the diodes.

The signal as modified by diode 408 includes two regions, non-truncated regions that represent a relative voltage level of the electrical power transduced from the energy signal and truncated regions that represent a reference voltage level (e.g., the forward voltage of diode 408). Transmit antenna 410 generates feedback signal 22 based on the modified signal. As one example, transmit antenna 410 may be a radiofrequency (RF) antenna that generates an RF signal with the waveform shown in FIG. 3. As another example, transmit antenna 410 may include a plurality of light emitting diodes that collectively generate the feedback signal. For instance, transmit antenna 410 may include a first light emitting diode that generates the first signal portion with an intensity that represents the relative power level and a second light emitting diode that generates the second signal portion with a reference intensity. In some of such examples, the external device may differentiate between the two light emitting diodes using a spatial distance between the diodes (e.g., the diodes may be mounted on IMD 20 a specified distance from each other). In this way, IMD 20 may generate a feedback signal that represents an absolute level of the electrical power transduced from the energy signal.

In addition to, or in place of, generating a feedback signal that represents the absolute level of the electrical power transduced from the energy signal, IMD 20 may generate a feedback signal that indicates an electrical current level of one or more components of IMD 20. As one example, IMD 20 may generate a feedback signal that represents the electrical current level of the output electrical stimulation waveform of electrodes 406. Current measurements in such instances may not be indicative of the voltage amplitude of an inductor in series with a piezoelectric power source (e.g., energy receiver 402). Instead, the current output may be used to modulate an in-series inductance, and therefore communicate the current level passively. One such example of this technique is to use an operational transconductance amplifier (OTA). By using an OTA, the current amplitude at a given portion of IMD 20 modulates the signal of an in-series truncated inductive signal (e.g., the signal as modified by diode 408) so that the amplitude is indicative of the current level.

In some examples, IMD 20 may be used for sensing conditions in the patient's body. Such conditions that may be sensed by IMD 20 include, but are not limited to, pH, glucose, oxygen, temperature, and pressure. In order to passively monitor these environmental conditions and passively communicate the measurements (e.g., to external device 40), IMD 20 may include one or more components to modulate the feedback signal based on levels of these conditions. For instance, IMD 20 may include one or more discreet elements that vary electrical behavior based levels of these conditions (e.g., thermistors vary resistance based on temperature) in series with the inductive signal (e.g., in series with energy receiver 402 and/or transmit antenna 410) to communicate varying levels.

Figure 5:
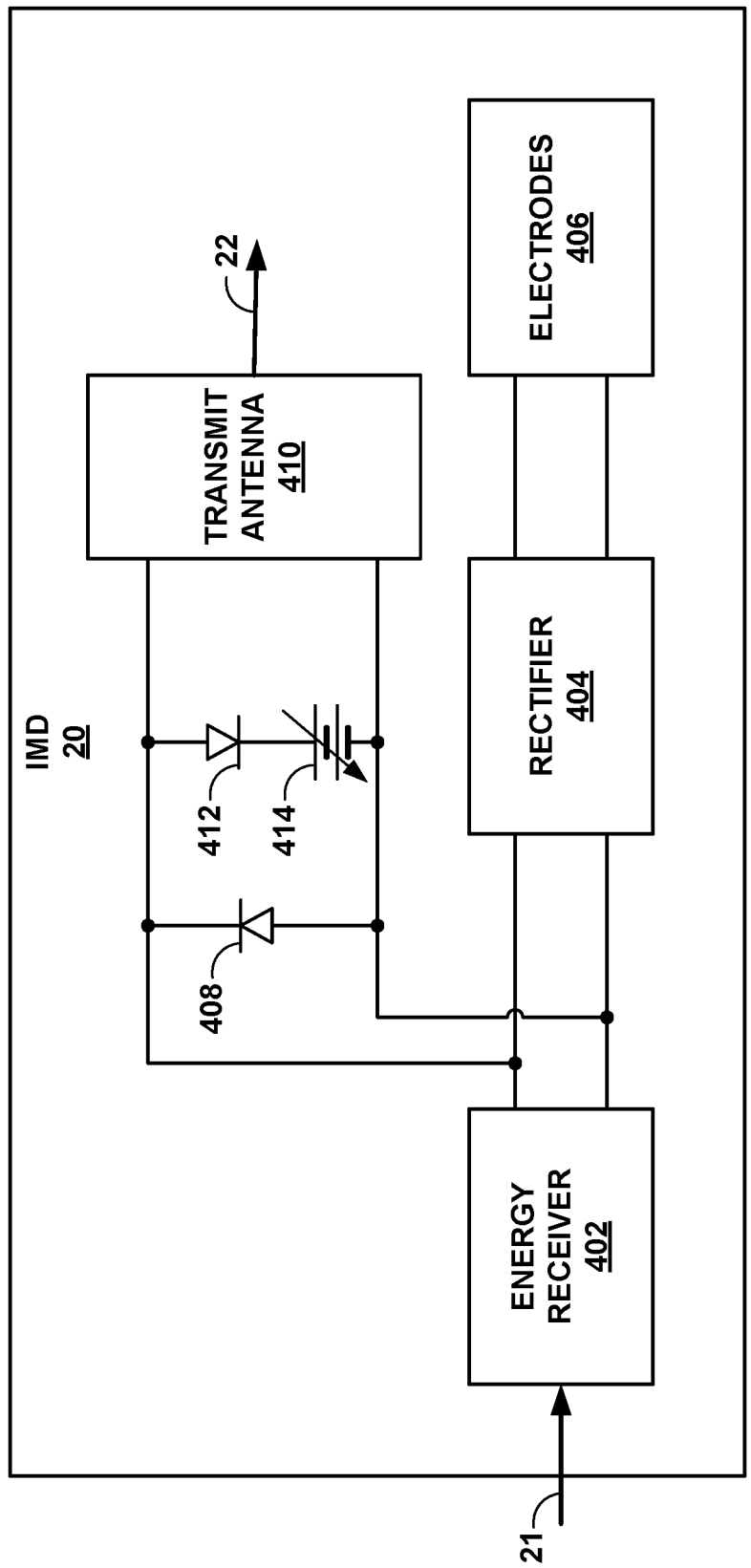
FIG. 5 is a block diagram illustrating further details of another example of an implantable medical device, in accordance with one or more techniques of this disclosure.

FIG. 5 is a block diagram illustrating further details of another example of an implantable medical device, in accordance with one or more techniques of this disclosure. As illustrated in FIG. 5, IMD 20 may include an energy receiver 402, a rectifier 404, one or more electrodes 406, a reference diode 408, a transmit antenna 410, a sense diode 412, and a sensor 414.

Sensor 414 may generate a voltage corresponding to a sensed value. For example, sensor 414 may include one or more of a pH, pressure, temperature, or other sensor that measures a value. Sensor 414 may convert the measured value into a voltage representative of the measured value (e.g., the voltage across sensor 414 changes in response to the measured value). As shown in FIG. 5, sensor 414 may be placed in series with sense diode 412 in order to cause a corresponding shift in the forward voltage. In some examples, the inclusion of sense diode 412 and sensor 414 may cause the first signal portion to be truncated by a level dictated by the measurement performed by sensor 414. Additionally, as shown in FIG. 5, the serial combination of sense diode 412 and sensor 414 may be electrically parallel to reference diode 408 such that sense diode 412 and reference diode 408 are opposite (or anti-parallel) of each other.

Figure 6:
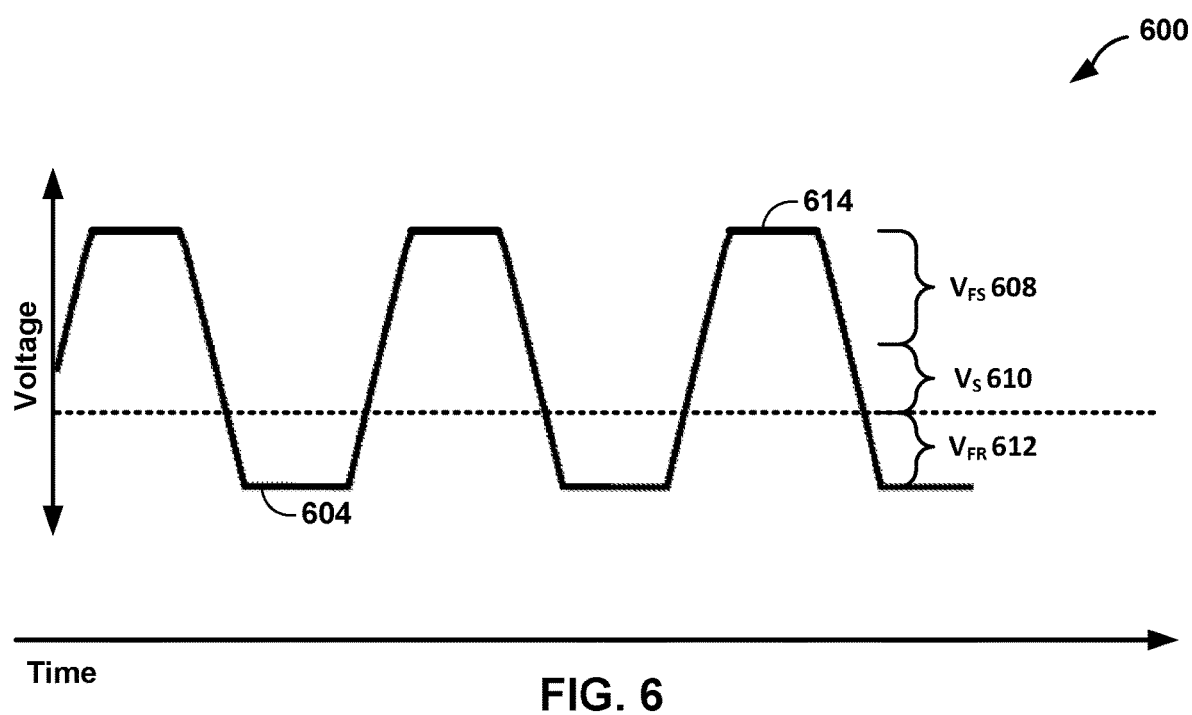
FIG. 6 is a graph illustrating another example feedback signal generated by an implantable medical device, in accordance with one or more techniques of this disclosure.

FIG. 6 is a graph illustrating another example feedback signal generated by an implantable medical device, in accordance with one or more techniques of this disclosure. Graph 600 may represent a feedback signal generated by an implantable medical device. For instance, graph 600 may represent feedback signal 22 generated by IMD 20 of FIG. 5. As can be seen from FIG. 6, the feedback signal may be periodic and may include truncation points (e.g., truncation point 604).

As discussed above, an implantable medical device, such as IMD 20, may generate a feedback signal that includes a first signal portion that represents a relative voltage level of the electrical power transduced from an energy signal by the IMD and a second signal portion that represents a reference voltage level. In some examples, in addition to or in place of representing a relative voltage level with a parameter of the first signal portion, an IMD may include a different parameter in the first or second signal portion in the feedback signal. The different parameter may represent a measurement sensed by a sensor of the IMD (e.g., a measurement sensed by sensor 414 of FIG. 5). As such, in some examples, the feedback signal may include three (or more) pieces of information. For example, the second signal portion may be truncation points 604 where the amplitude (a first parameter) represents the reference voltage level, the first signal portion may be truncation points 614 where the amplitude (a second parameter) represents the measurement sensed by the sensor of the IMD, and the first signal portion can also convey information about the relative voltage level by way of the duration of the truncated portion 604. In this manner, the portions can represent respective temporal sections of a signal, where each temporal section can convey one or more pieces of information. As discussed above, the various signal portions may be non-overlapping such that a single signal portions occurs at any one time.

Various aspects of the feedback signal are marked on FIG. 6. In particular, the forward voltage of a sense diode (e.g., the forward voltage of sense diode 412 of FIG. 5) is marked as $V_{FS}$ 608, the voltage across a sensor (e.g., the voltage across sensor 414 of FIG. 5) is marked as $V_S$ 610, and the forward voltage of a reference diode (e.g., the forward voltage of reference diode 408 of FIG. 5) is marked as VFR 612.

As shown by FIG. 6, the values of the peaks of the feedback signal e.g., truncations points 614) are the sum of the value of $V_S$ 610 and $V_{FS}$ 608. The portions of the feedback signal that are the sum of the sense diode forward voltage and the sensor voltage may be referred to as the third signal portion discussed above.

Figure 7:
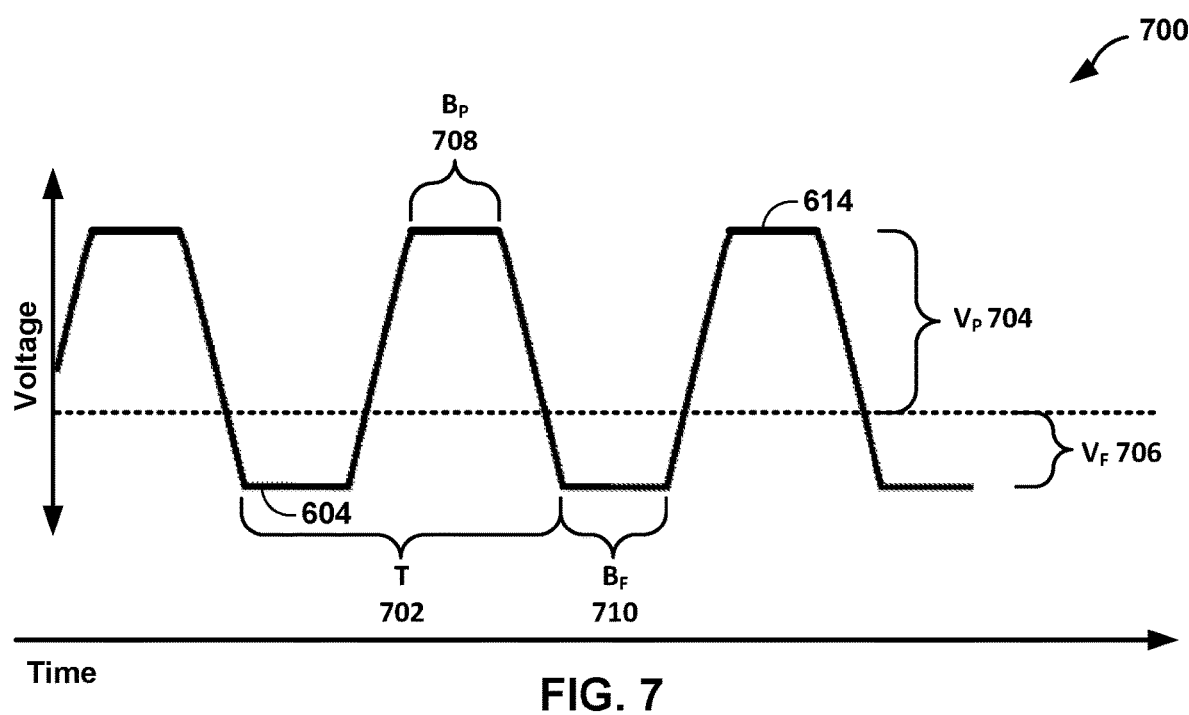
FIG. 7 is a graph illustrating another example feedback signal generated by an implantable medical device, in accordance with one or more techniques of this disclosure.

FIG. 7 is a graph illustrating another example feedback signal generated by an implantable medical device, in accordance with one or more techniques of this disclosure. Graph 700 may represent the same feedback signal as graph 600 of FIG. 6. For instance, graph 700 may represent feedback signal 22 generated by IMD 20 of FIG. 5 that includes a parameter of a first signal portion (e.g., the voltage at truncation point 614) that represents a measurement sensed by a sensor of IMD 20, a parameter of a second signal portion (e.g., the voltage truncation point 604) that represents a reference voltage level of IMD 20, and further parameters of the first, second, or both first and second signal portions that represents a relative level of electrical power transduced by IMD 20. For instance, the parameter(s) representing the relative level of electrical power transduced can be the durations of truncation points 614 or 604.

Various aspects of the feedback signal are marked on FIG. 7. In particular, the period of the feedback signal is marked as T 702, the peak voltage of the first signal portion (e.g., $V_S$ 610 plus $V_{FS}$ 608 of FIG. 6) is marked as $V_P$ 704, the peak voltage of the second signal portion (e.g., the forward voltage of reference diode 408 of FIG. 5) is marked as $V_F$ 706, the time duration of the first signal portion is marked as $B_P$ 708, and the time duration of the second signal portion is marked as $B_F$ 710.

Figure 8:
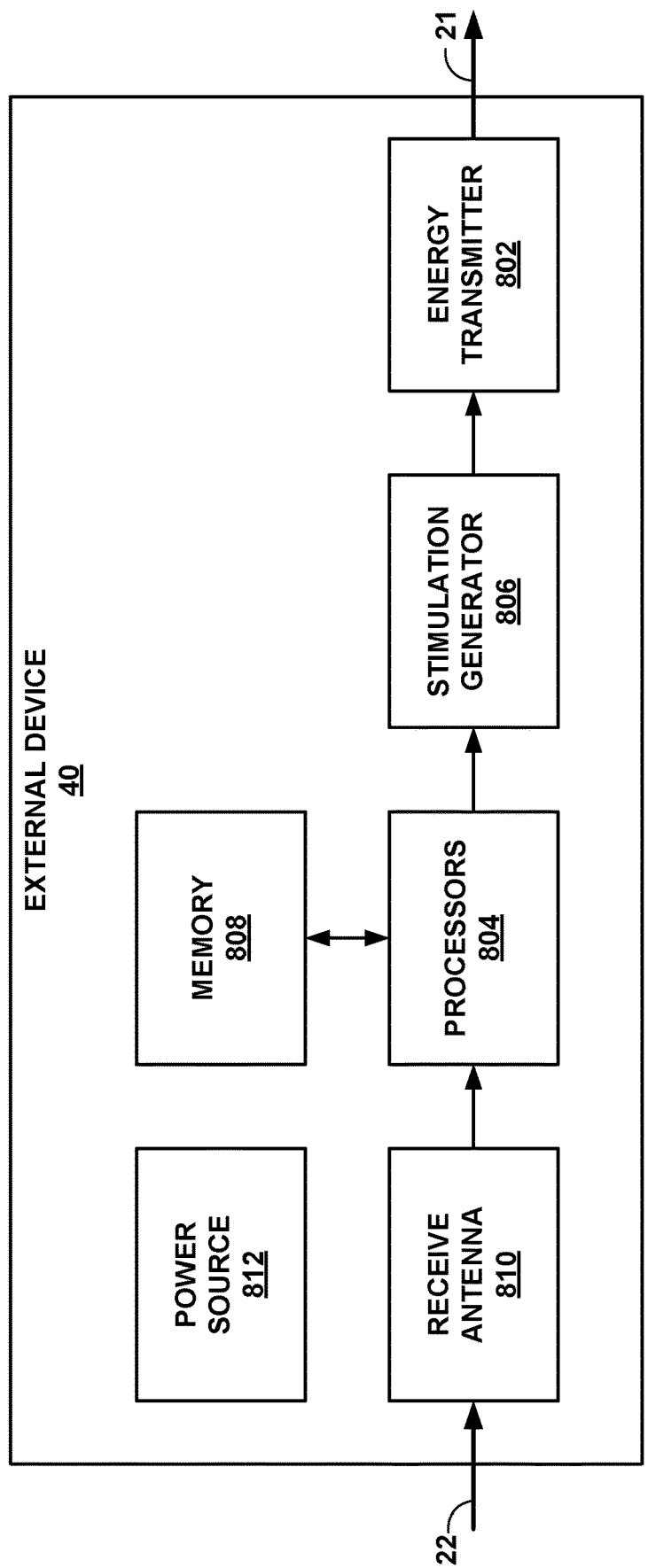
FIG. 8 is a block diagram illustrating further details of one example of an external device, in accordance with one or more techniques of this disclosure.

FIG. 8 is a block diagram illustrating further details of one example of an external device, in accordance with one or more techniques of this disclosure. As illustrated in FIG. 8, external device 40 may include an energy transmitter 802, one or more processors 804, a stimulation generator 806, memory 808, a receive antenna 810, and a power source 812.

Memory 808 may store instructions for execution by processors 804, stimulation therapy data, sensor data, and/or other information regarding therapy for a patient. Processors 804 may control stimulation generator 806 to operate according to a selected one or more of a plurality of programs or program groups stored in memory 808. Memory 808 may include any electronic data storage media, such as random-access memory (RAM), read-only memory (ROM), electronically-erasable programmable ROM (EEPROM), flash memory, or the like. Memory 808 may store program instructions that, when executed by processors 804, cause the processors to perform various functions ascribed to processors 804 and external device 40 in this disclosure. In some examples, memory 808 may store one or more characteristics of an implantable medical device. For example, memory 808 may store (e.g., be preprogrammed with in advance of a therapy session) a forward voltage of a diode of an implantable medical device (e.g., $V_F$ of diode 408 of IMD 20 of FIG. 4).

Processors 804 may include one or more microprocessors, digital signal processors (DSPs), application-specific integrated circuits (ASICs), field-programmable gate arrays (FPGAs), or other digital logic circuitry. Processors 804 control operation of external device 40, e.g., controls external device 40 to output energy signals that cause an implantable medical device to deliver stimulation therapy according to a selected program or group of programs retrieved from memory 808. For example, processors 804 may control stimulation generator 806 to generate electrical signals, e.g., as stimulation pulses or continuous waveforms, with current amplitudes, pulse widths (if applicable), and rates specified by one or more stimulation programs.

Stimulation generator 806 may include stimulation generation circuitry to generate stimulation pulses or waveforms, e.g., in response to control by processors 804. Stimulation generator 806 produces an electrical stimulation signal in accordance with a program based on control signals from processors 804. As discussed above, external device 40 may not directly deliver stimulation to the patient. Instead, external device 40 may generate the stimulation waveforms (e.g., the electrical stimulation signals) as an energy signal delivered to IMD 20 and cause the IMD to actually deliver the stimulation to the patient. For instance, stimulation generator 806 may output the stimulation signals to energy transmitter 802 for output to IMD 20 as an energy signal. As discussed herein, an implantable device, such as IMD 20 of FIG. 1 or FIG. 4, may not include a stimulation generator similar to power source 812.

Hence, energy transmitter 802 may be configured to generate, output, or otherwise transmit energy signals. For instance, energy transmitter 802 may be configured to convert the stimulation signals generated by stimulation generator 806 into energy signals 21, and output the resulting energy signals 21 for receipt by an implantable device, such as IMD 20 of FIG. 1. In some examples, such as where energy signals 21 include ultrasound signals, energy transmitter 802 may include piezoelectric material that generates the ultrasound signals.

Energy transmitter 802 may be configured to focus energy signals 21 at a specific 3-dimensional location within the patient. For instance, energy transmitter 802 may include an array of phase-controlled emitters capable of focusing energy signals at a specific 3-dimensional location. As one example, energy transmitter 802 may include a plurality of ultrasound emitters. As another example, energy transmitter 802 may include a plurality of antennas (e.g., where the energy signal is an RF signal).

Power source 812 delivers operating power to the components of external device 40. Power source 812 may be a rechargeable battery, such as a lithium ion or nickel metal hydride battery. Other rechargeable or conventional batteries may also be used. In some cases, external device 40 may be used when coupled to an alternating current (AC) outlet, e.g., AC line power, either directly or via an AC/DC adapter. As discussed herein, an implantable device, such as IMD 20 of FIG. 1 or FIG. 4, may not include a power source similar to power source 812.

As discussed above, the implantable device that receives energy signals 21 (e.g., IMD 20 of FIG. 1 or FIG. 4) may transduce energy signals 21 into electrical power and deliver a level of electrical stimulation proportional to a level of the electrical power transduced from the energy signal. Additionally, the location of the implantable device in relation to external device 40, and thus the amount of power transduced by the implantable device, may change. As such, it may be desirable for external device 40 to be able to determine how much power is being received by the implantable device.

In accordance with one or more techniques of this disclosure, external device 40 may include receive antenna 810, which may be configured to receive a feedback signal from the implantable device that represents an absolute level of the electrical power that the implantable device transduced from the energy signals output by external device 40. For instance, receive antenna 810 may receive feedback signal 22 from IMD 20. In some examples, receive antenna 810 may be a radiofrequency (RF) antenna that wirelessly receives a feedback signal 22 transmitted wirelessly from an antenna of IMD 20.

Different electronic components may have various levels of ability to transmit inductively. To avoid the need to redesign the transducer's inductive antenna to have different inductive strengths, receive antenna 810 may include a flex circuit that provides modular stackability. For instance, receive antenna 810 may include a thin film inductor having connector pads arranged so that multiple of the same antenna can simply be stacked on top of each other to increase inductance and ability to receive weaker signal strength. These antenna flex boards can be a singular concentric loop or contain multiple smaller loops.

Processors 804 may process the feedback signal to determine the absolute level of the electrical power that the implantable device transduced from the energy signals. For instance, processors 804 may identify a first signal portion of the feedback signal that that represents a relative level (e.g., a shape of the electrical power, but not an absolute level) of the transduced electrical power and a second signal portion of the feedback signal that represents a reference voltage level. In some examples, processors 804 may identify the first signal portion of the feedback signal as a portion of the feedback signal that is not truncated and identify the second signal portion of the feedback signal as a portion of the feedback signal that is truncated (e.g., truncated region 304 of FIG. 3). Processors 804 may obtain a value of the reference voltage level. For instance, processors 804 may receive, from memory 808, the value of the reference voltage level.

Based on the value of the reference voltage level and the first portion of the feedback signal, processors 804 may calculate the absolute level of the electrical power that the implantable device transduced from the energy signals. In some examples, processors 804 may scale the non-truncated regions of feedback signal 22 based on the value of the reference voltage level. In some examples, processors 804 may calculate the absolute level of the electrical power in accordance with the following equations:

$$P_{average} = \frac{V_{RMS}^2}{Z_{implant}}$$

$$V_{RMS} = \sqrt{\frac{1}{T}\int_0^T V(t)^2 dt} \approx \sqrt{\frac{V_P^2}{4} + V_F^2\left(\frac{\frac{T}{2}-B}{3T}\right) + V_F^2\left(\frac{B}{T}\right)}$$

wherein $P_{average}$ is the average power transduced by the implantable device, $V_{RMS}$ is the RMS voltage transduced by the implantable device, $Z_{Implant}$ is the impedance of the implantable device (which may be known to external device 40), T is the period (e.g., T 306 of FIG. 3), $V_P$ is the peak voltage of first signal portion (e.g., $V_P$ 308 of FIG. 3), $V_F$ is the forward voltage of the diode (e.g., the forward voltage of diode 408 or $V_F$ 310 of FIG. 3), and B is the time duration of diode clipping (e.g., B 312 of FIG. 3).

In other examples, such as where the feedback signal includes a parameter of the first signal portion that represents a value of a measured condition, processors 804 may calculate the absolute level of the electrical power in accordance with the following equations:

$$P_{average} = \frac{V_{RMS}^2}{Z_{implant}}$$

$$V_{RMS} = \sqrt{\frac{1}{T}\int_0^T V(t)^2 dt} \approx \sqrt{V_P^2\left(\frac{B_P}{T}\right) + V_P^2\left(\frac{\frac{T}{2}-B_P}{3T}\right) + V_F^2\left(\frac{B_F}{T}\right) + V_F^2\left(\frac{\frac{T}{2}-B_F}{3T}\right)}$$

wherein $P_{average}$ is the average power transduced by the implantable device, $V_{RMS}$ is the RMS voltage transduced by the implantable device, $Z_{Implant}$ is the impedance of the implantable device (which may be known to external device 40), T is the period (e.g., T 702 of FIG. 7), $V_P$ is the peak voltage of first signal portion (e.g., $V_P$ 704 of FIG. 7), $V_F$ is the forward voltage of the diode (e.g., the forward voltage of diode 408 or $V_F$ 706 of FIG. 7), $B_P$ is the time duration of first signal portion clipping (e.g., $B_P$ 708 of FIG. 7), $B_F$ is the time duration of second signal portion clipping (e.g., $B_F$ 710 of FIG. 7).

Processors 804 may control operation of stimulation generator 806 based on the determined absolute level of the electrical power that the implantable device transduced from the energy signals. For instance, processors 804 may utilize the determined absolute level of the electrical power to effectuate closed-loop control over the amount of stimulation delivered by the implantable device.

In some examples, external device 40 may utilize the feedback signal to locate the implantable device. For instance, external device 40 may search a volume of space by sweeping a target of the energy signals. In some examples, external device 40 may sweep a target by causing energy transmitter 802 to focus energy signals 21 at various target locations. External device 40 may perform sweeping (or rastering) using a variety of patterns. Example patterns include, but are not limited to, a row-by-row in either a "z" or "s" pattern, a spiral pattern, or some other methodical method that covers all space in a volume, such as beam-forming across a volume (e.g., to search along directions rather than searching at a specific point).

External device 40 may use these patterns either forward or in reverse order, combined in conjunction with each other, and be treated with layers in any orientation in a 3-dimensional space. While sweeping the target, external device 40 may maintain a particular level of the energy signals 21. For each target location, external device 40 may receive a feedback signal and determine an absolute amount of power transduced by the implantable device. External device 40 may identify the target location that results in the greatest absolute amount of power as the location of the implantable device.

External device 40 may perform rastering spherically, or even randomly or semi-randomly by moving the focal point to positions not in a pattern. The raster of the focal point may also be done deterministically, where selection of a future raster location may be based on received responses from one or multiple previous raster locations in the interest of quicker searching. External device 40 may continue the rastering until the conclusion of the full volume, or may terminate the rastering based on feedback received during the raster (e.g., if the implantable device is located, external device 40 may cease rastering).

Once the location of the implantable device is determined, external device 40 may output energy signals to the determined location. For instance, processors 804 may cause energy transmitter 802 to focus energy signals 21 at the determined location. As one example, where energy transmitter 802 includes a spatial array of transmitters, processors 804 may cause different transmitters in the array to output energy signals at different phases such that a majority (or all) of the energy signals are in-phase with each other at the determined location.

External device 40 may use rastering of an ultrasound focal point to simulate a larger focal point. If a focal point's size is small, but the intended target requires larger coverage, the focal point can be rastered over a set volume or area. External device 40 may perform rastering continuously where the focal point is repeatedly rastered in a repeated pattern over a set volume. External device 40 may repeat the pattern, or each use a different pattern for each iteration. External device 40 may cycle the rastering iterations continuously, or intermittently. and the rastering may keep the same volume each iteration, or may change volume. If external device 40 changes the volume per iteration, this change may be per a prescribed pattern such as an increasing and/or decreasing pattern. The change may also be random or deterministic based on feedback received by external device 40 during previous iterations. External device 40 may continue iterating or rastering within a given iteration indefinitely, until a completion of a set pattern or iteration count, or may be terminated based on received feedback.

In some examples, external device 40 may be configured to locate the implantable device while therapy is being delivered. In some examples, external device 40 may be configured to locate the implantable device while therapy is not being delivered.

As discussed above, in some examples, the feedback signal received by external device 40 may include sensor measurements made by one or more sensors of the implantable device. For example, feedback signal 22 may include a parameter of a first signal portion with a truncation point (e.g., voltage at truncation point 614 of FIG. 6) that represents a combined forward voltage across a sense diode and a sensor voltage. External device 40 may store a predetermined value of the forward voltage across the sensor diode and use this predetermined value to determine an actual value of the sensor voltage. External device 40 may then convert the actual value of the sensor voltage into a value of the measurement made by the sensor of the implantable device.

As discussed above, in some examples, the implantable device may include multiple receiver/rectifier/transmit pathways within the housing to allow multiple channels of stimulation through different sets of electrodes. In some of such examples, external device 40 may utilize the locating techniques described above to determine locations of the receivers of the different pathways. For instance, external device 40 may perform the rastering to identify the locations that result in generation of the unique feedback signals of each of the various pathways of the implantable device.

Figure 9:
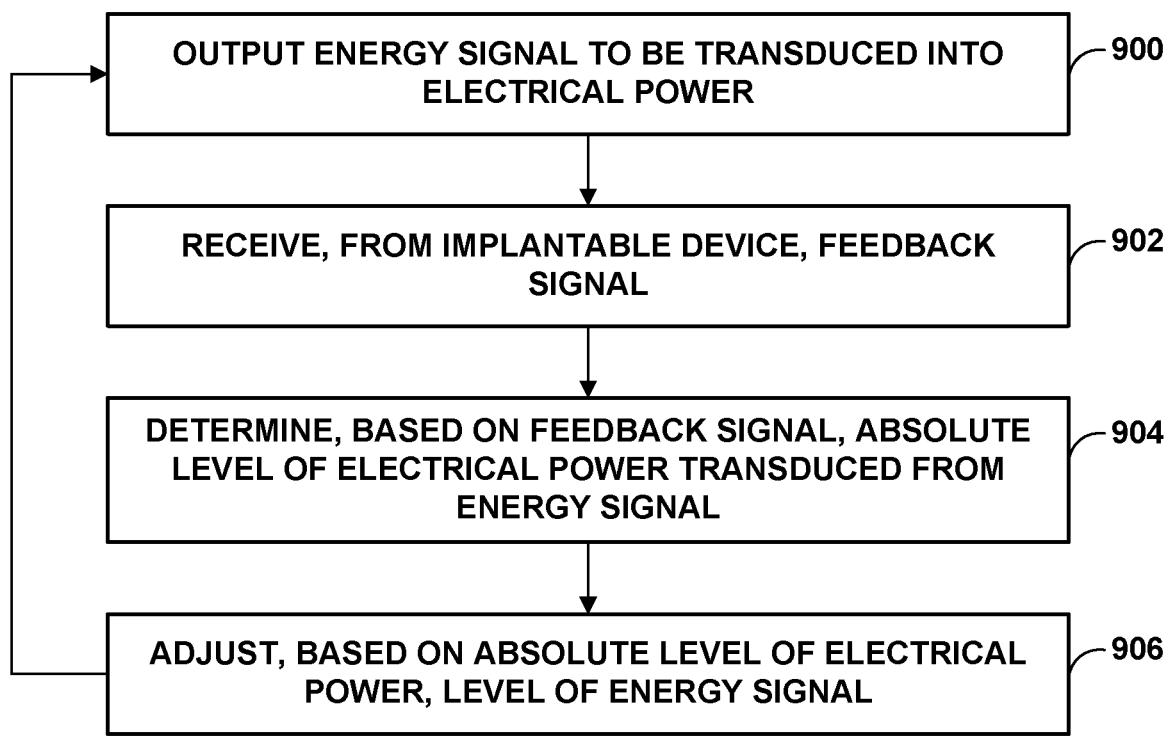
FIG. 9 is a flow diagram illustrating example operations of an external device to control the amount of therapy provided by an implantable medical device, in accordance with one or more techniques of this disclosure.

FIG. 9 is a flow diagram illustrating example operations of an external device to control the amount of therapy provided by an implantable medical device, in accordance with one or more techniques of this disclosure. For purposes of explanation, the techniques of FIG. 9 are described with reference to external device 40 of FIGS. 1 and 8, though other external devices may perform the techniques of FIG. 9.

External device 40 may output an energy signal to be transduced into electrical power by an implantable device that delivers a level of electrical stimulation therapy proportional to a level of the electrical power transduced from the energy signal (900). For instance, processors 804 of external device 40 may cause stimulation generator 806 to generate and output electrical stimulation waveforms to energy transmitter 802, which may output energy signals 21 in accordance with the stimulation waveforms. As discussed above, in some examples, energy signals 21 may be ultrasound waves focused at a 3-dimensional point in a patient identified by external device 40 as corresponding to the implantable device (e.g., IMD 20 of FIG. 1).

External device 40 may receive, from the implantable device, a feedback signal (902). For instance, processors 804 may receive, via receive antenna 810, a feedback signal having a first portion that represents a relative level of the electrical power transduced from the energy signal and a second portion that represents a reference voltage level. As discussed above, in some examples, the feedback signal may be a radio frequency (RF) signal. The ratio of the first portion to the second portion is proportional to the amplitude of the energy received by the implantable device.

External device 40 may determine, based on the feedback signal, an absolute level of electrical power transduced from the energy signal (904). For instance, processors 804 may obtain a value of the reference voltage level and calculate, based on the reference voltage level and the relative level of the electrical power transduced from the energy signal, the absolute level of electrical power transduced from the energy signal. As discussed above, in some examples, the value of the reference voltage level may correspond to a voltage of a diode included in the implantable device and may be pre-determined (e.g., may be "known" to external device 40 without being received from the implantable device). For instance, the second portion of the feedback signal may be generated by the diode, which may be electrically parallel across an antenna of the implantable device that transmits the feedback signal.

External device 40 may adjust, based on the determined absolute level of electrical power, a level of the energy signal (906). For instance, external device 40 may adjust a duration and/or intensity of the energy signal. As one example, if the determined absolute level indicates that the implantable device is not transducing enough power (and thus delivering stimulation therapy with less than a desired intensity), processors 804 may cause stimulation generator 806 to increase a magnitude of the waveforms. As another example, if the determined absolute level indicates that the implantable device is transducing too much power (and thus delivering stimulation therapy with more intensity than desired), processors 804 may cause stimulation generator 806 to decrease a magnitude of the waveforms. As another example, if the determined absolute level indicates that the implantable device is transducing a correct amount power (and thus delivering the correct amount of therapy), e.g., when the absolute level resides in a desired range, processors 804 may cause stimulation generator 806 to not change a magnitude of the waveforms.

While described above as being used to determine the absolute power level of the electrical signal transduced from the energy signal, the techniques of this disclosure may be applicable to other variables. For instance, external device 40 may generally receive a feedback signal that includes a first portion that represents a variable feedback input and a second portion that represents a reference voltage level. External device 40 may determine, based on the feedback signal, the value of the variable feedback input. The variable feedback input may be any variable at the implantable device. As one example, the variable feedback input may be the absolute power level of the electrical signal transduced from the energy signal. As another example, the variable feedback input may be a value of a measurement made by a sensor of the implantable device. As discussed above, in some examples, the feedback signal may include multiple portions that each represent a separate variable feedback input. For instance, the feedback signal may include a first parameter of a first portion that represents a first variable feedback input (e.g., the absolute power level), a parameter of a second portion that represents a reference voltage level, and another parameter of the first portion that represents a second variable feedback input (e.g., the value of the measurement).

Figure 10:
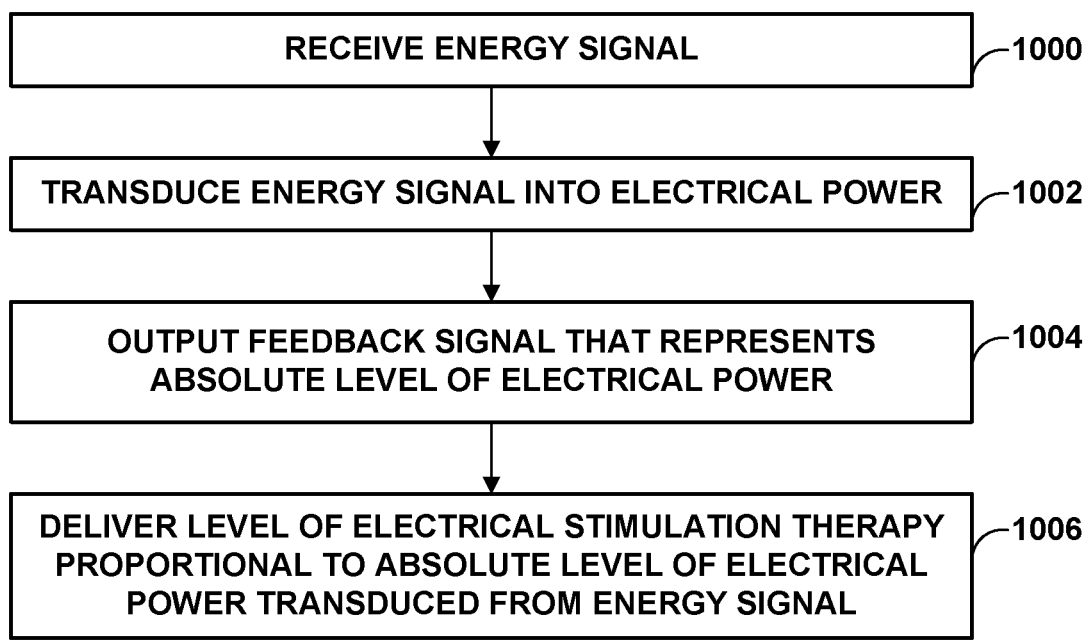
FIG. 10 is a flow diagram illustrating example operations of an implantable medical device, in accordance with one or more techniques of this disclosure.

FIG. 10 is a flow diagram illustrating example operations of an implantable medical device, in accordance with one or more techniques of this disclosure. For purposes of explanation, the techniques of FIG. 10 are described with reference to IMD 20 of FIGS. 1 and 4, though other implantable medical devices may perform the techniques of FIG. 10.

IMD 20 may be implanted in a patient. For instance, as discussed above, IMD 20 may be injected proximal to a tibial nerve of the patient.

IMD 20 may receive an energy signal (1000). For instance, energy receiver 402 of IMD 20 may receive energy signals 21 from an external device, such as external device 40 of FIG. 1. As discussed above, in some examples, the energy signal may include an ultrasound signal.

IMD 20 may transduce the energy signal into electrical power (1002). For instance, energy receiver 402 may include piezoelectric material that converts energy signals 21 into electrical power.

IMD 20 may output a feedback signal that represents an absolute level of the electrical power (1004). For instance, diode 408 and transmit antenna 410 may collectively generate and output feedback signal 22 that includes a first portion that represents a relative level of the electrical power transduced from the energy signal and a second portion that represents a reference voltage level. As discussed above, the reference voltage level may be a forward voltage of diode 408. In some examples, the feedback signal output by IMD 20 may be a radio frequency (RF) signal.

In some examples, the absolute level of the electrical power calculable from the feedback signal may differ slightly from the absolute level of the electrical power transduced from the energy signal (e.g., due to circuit losses or other signal conditioning). As such, in some examples, the relative level of the electrical power transduced from the energy signal represented by the first portion may be a relative level of the electrical power at a transmitter of IMD 20.

IMD 20 may deliver, to the patient, a level of electrical stimulation therapy proportional to the absolute level of the electrical power transduced from the energy signal (1006). For instance, IMD 20 may deliver electrical stimulation therapy with a magnitude that corresponds to the absolute level of the electrical power transduced from the energy signal. In some examples, the magnitude of the delivered electrical stimulation therapy may differ slightly from the absolute level of the electrical power transduced from the energy signal (e.g., due to circuit losses or other signal conditioning). As discussed above with reference to FIG. 2, in addition to the magnitude, the pulse width and pulse rate of the delivered electrical stimulation therapy may correspond to the pulse width and pulse rate of the energy signal and therefore the electrical power transduced from the energy signal.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
wirelessly outputting, by an external device, an energy signal to be transduced into electrical power by an implantable device that delivers a level of electrical stimulation therapy proportional to a level of the electrical power transduced from the energy signal;
wirelessly receiving, by the external device and from the implantable device, a feedback signal having a first temporal portion that represents a relative voltage level of the electrical power transduced from the energy signal and a second temporal portion that represents a reference voltage level, wherein the first temporal portion and the second temporal portion are non-overlapping in time, and wherein the reference voltage level corresponds to a voltage across a diode of the implantable device;

determining, by the external device and based on the first temporal portion and the second temporal portion of the feedback signal, an absolute level of the electrical power transduced from the energy signal;

adjusting, by the external device and based on the determined absolute level of the electrical power, a level of the energy signal to control the level of electrical stimulation therapy delivered by the implantable device, wherein adjusting the level of the energy signal comprises decreasing the level of the energy signal to reduce the level of the electrical stimulation therapy delivered by the implantable device; and outputting, by the external device, the energy signal with the adjusted level.

2. The method of claim 1, wherein the energy signal comprises an ultrasound signal, and wherein receiving the feedback signal comprises receiving a radio frequency (RF) signal.

3. The method of claim 1, wherein the energy signal comprises a radio frequency (RF), and wherein receiving the feedback signal comprises receiving another RF signal.

4. The method of claim 1, further comprising:
determining a location of the implantable device, wherein outputting the energy signal comprises outputting the energy signal to the determined location.

5. The method of claim 4, wherein determining the location of the implantable device comprises:
outputting energy signals to a plurality of respective target locations;
receiving, for each respective target location, a respective feedback signal of a plurality feedback signals; and
identifying, based on the plurality of feedback signals, a particular location of the plurality of target locations as the location of the implantable device.

6. The method of claim 1, wherein a first parameter of the first temporal portion of the feedback signal represents the relative voltage level of the electrical power transduced from the energy signal and a second parameter of the first temporal portion of the feedback signal represents a value of a measurement made by a sensor of the implantable device, the method further comprising:
determining, based on the second parameter of the first temporal portion of the feedback signal, the value of the measurement.

7. An external device comprising:
a transmitter configured to wirelessly output an energy signal to be transduced into electrical power by an implantable device that delivers a level of electrical stimulation therapy proportional to a level of the electrical power transduced from the energy signal;
a receiver configured to wirelessly receive, from the implantable device, a feedback signal having a first temporal portion that represents a relative voltage level of the electrical power transduced from the energy signal and a second temporal portion that represents a reference voltage level, wherein the first temporal portion and the second temporal portion are non-overlapping in time, and wherein the reference voltage level corresponds to a voltage across a diode of the implantable device; and
one or more processors configured to:
determine, based on the first temporal portion and the second temporal portion of the feedback signal, an absolute voltage level of the electrical power transduced from the energy signal;
adjust, based on the determined absolute voltage level of the electrical power, a level of the energy signal to control the level of electrical stimulation therapy delivered by the implantable device, wherein, to adjust the level of the energy signal, the one or more processors are configured to decrease the level of the energy signal to reduce the level of the electrical stimulation therapy delivered by the implantable device; and
cause the transmitter to output the energy signal with the adjusted level.

8. The external device of claim 7, wherein the energy signal comprises an ultrasound signal, the transmitter comprises one or more ultrasound emitters, receiving the feedback signal comprises receiving a radio frequency (RF) signal, and the receiver comprises one or more RF antennas.

9. The external device of claim 7, wherein the energy signal comprises a radio frequency (RF) signal, the transmitter comprises one or more RF emitters, receiving the feedback signal comprises receiving another RF signal, and the receiver comprises one or more RF antennas.

10. The external device of claim 7, wherein the voltage across the diode is a forward voltage across the diode of the implantable device.

11. The external device of claim 7, wherein the one or more processors are further configured to determine a location of the implantable device, and the transmitter is configured to output the energy signal to the determined location.

12. The external device of claim 11, wherein, to determine the location of the implantable device, the one or more processors are configured to:
cause the transmitter to output energy signals to a plurality of respective target locations;
receive, via the receiver and for each respective target location, a respective feedback signal of a plurality feedback signals; and
identify, based on the plurality of feedback signals, a particular location of the plurality of target locations as the location of the implantable device.

13. The external device of claim 7, wherein a first parameter of the first temporal portion of the feedback signal represents the relative voltage level of the electrical power transduced from the energy signal and a second parameter of the first temporal portion of the feedback signal represents a value of a measurement made by a sensor of the implantable device, and wherein the one or more processors are further configured to:
determine, based on the second parameter of the first temporal portion of the feedback signal, the value of the measurement.

14. A method comprising:
wirelessly receiving, by an implantable device and from an external device, an energy signal;
transducing, by the implantable device, the energy signal into electrical power;
generating, from the electrical power, a feedback signal that includes a first temporal portion that represents a variable feedback input and a second temporal portion that represents a reference voltage level, wherein the first temporal portion and the second temporal portion are non-overlapping in time, and wherein the reference voltage level corresponds to a voltage across a diode of the implantable device;

wirelessly outputting, by the implantable device and to the external device, the feedback signal; and delivering, by the implantable device, a level of electrical stimulation therapy proportional to an absolute voltage level of the electrical power transduced from the energy signal such that the implantable device delivers a reduced level of the electrical stimulation therapy in response to transducing a decreased absolute voltage level of the electrical power.

15. The method of claim 14, wherein the variable feedback input comprises a relative voltage level of the electrical power transduced from the energy signal, and wherein generating the feedback signal comprises:

setting an amplitude of a first parameter of the first temporal portion of the feedback signal to represent the relative voltage level of the electrical power level.

16. The method of claim 15, further comprising:

generating, by a sensor of the implantable device, a value of a measurement, wherein generating the feedback signal further comprises:

setting an amplitude of a second parameter of the first temporal portion of the feedback signal to represent the value of the measurement.

17. The method of claim 14, further comprising:

generating, by a sensor of the implantable device, a value of a measurement, wherein generating the feedback signal comprises:

setting an amplitude of the first temporal portion of the feedback signal to represent the value of the measurement.

18. The method of claim 14, wherein receiving the energy signal comprises receiving an ultrasound signal, and wherein outputting the feedback signal comprises outputting a radio frequency (RF) signal.

19. The method of claim 14, wherein receiving the energy signal comprises receiving a radio frequency (RF) signal, and wherein outputting the feedback signal comprises outputting another RF signal.

20. The method of claim 14, wherein the voltage across the diode is a forward voltage across the diode of the implantable device.

21. An implantable device comprising:

a receiver configured to wirelessly receive, from an external device, an energy signal;

a transducer configured to convert the energy signal into electrical power;

a feedback signal generator configured to generate, from the electrical power, a feedback signal that includes a first temporal portion that represents a variable feedback input and a second temporal portion that represents a reference voltage level, wherein the first temporal portion and the second temporal portion are non-overlapping in time, and wherein the reference voltage level corresponds to a voltage across a diode of the implantable device;

a transmitter configured to output, to the external device, the feedback signal; and circuitry and one or more electrodes collectively configured to deliver electrical stimulation therapy with an amplitude that is proportional to an absolute voltage level of the electrical power transduced from the energy signal, wherein the circuitry is configured to deliver a reduced level of the electrical stimulation therapy when the transducer transduces a decreased voltage level of the electrical power.

22. The implantable device of claim 21, wherein the variable feedback input comprises a relative voltage level of the electrical power transduced from the energy signal, and wherein, to generate the feedback signal, the feedback signal generator is configured to:

set an amplitude of a first parameter of the first temporal portion of the feedback signal to represent the relative voltage level of the electrical power.

23. The implantable device of claim 22, further comprising:

a sensor configured to measure a condition of a patient in which the implantable device is implanted, wherein the variable feedback input comprises a value of the measured condition, and wherein, to generate the feedback signal, the feedback signal generator is further configured to:

set an amplitude of a second parameter of the first temporal portion of the feedback signal to represent the value of the measured condition.

24. The implantable device of claim 21, further comprising:

a sensor configured to measure a condition of a patient in which the implantable device is implanted, wherein the variable feedback input comprises a value of the measured condition, and wherein, to generate the feedback signal, the feedback signal generator is configured to:

set an amplitude of first temporal portion of the feedback signal to represent the value of the measured condition.

25. The implantable device of claim 21, wherein the energy signal comprises an ultrasound signal, the receiver comprises a receiver configured to receive the ultrasound signal, the feedback signal comprises a radio frequency (RF) signal, and wherein the transmitter comprises an RF transmitter.

26. The implantable device of claim 21, wherein the energy signal comprises a radio frequency (RF) signal, the receiver comprises an RF receiver configured to receive the RF signal, the feedback signal comprises another RF signal, and wherein the transmitter comprises an RF transmitter.

27. The implantable device of claim 21, wherein the voltage across the diode is a forward voltage across the diode.

28. The implantable device of claim 21, wherein the implantable device does not include either a stimulation generator or a power source.

29. A system comprising:

an external device configured to output an energy signal;

an implantable device configured to:

measure a condition of a patient in which the implantable device is implanted;

transduce the energy signal into electrical power;

output a feedback signal that represents an absolute voltage level of the electrical power transduced from the energy signal, wherein the feedback signal includes:

a first temporal portion having a first parameter that represents a relative voltage level of the electrical power transduced from the energy signal and a second parameter that represents a value of the measured condition, and a second temporal portion that represents a reference voltage level, wherein the first temporal portion and the second temporal portion are non-overlapping in time, and wherein the reference voltage level corresponds to a voltage across a diode of the implantable device; and deliver a level of electrical stimulation therapy proportional to the absolute voltage level of the electrical power transduced from the energy signal such that the implantable device delivers a reduced level of the electrical stimulation therapy in response to transducing a decreased level of the electrical power, wherein the external device is further configured to:
determine, based on the second parameter of the first temporal portion of the feedback signal, the value of the measured condition;
determine, based on the first temporal portion and the second temporal portion of the feedback signal, the absolute voltage level of the electrical power transduced from the energy signal;
adjust, based on the determined absolute voltage level of the electrical power, a level of the energy signal; and
output the energy signal with the adjusted level.

30. The system of claim 29, wherein the energy signal comprises an ultrasound signal, and wherein the feedback signal comprises a radio frequency (RF) signal.

31. The system of claim 29, wherein the energy signal comprises a radio frequency (RF) signal, and wherein the feedback signal comprises another RF signal.

32. The system of claim 29, wherein the voltage across the diode is a forward voltage across the diode, and wherein the external device comprises a memory that is pre-programmed with the reference voltage level.

33. The system of claim 29, wherein the measured condition of the patient includes one or more of a pH level, a glucose level, an oxygen level, a temperature level, and a pressure level.

34. A method comprising:
receiving, by an implantable device and from an external device, an energy signal, wherein the implantable device does not include a stimulation generator and does not include a power source;
transducing, by the implantable device, the energy signal into an electrical signal;
measuring, by a sensor of the implantable device, a condition of a patient in which the implantable device is implanted;
generating, from the electrical signal, a feedback signal by setting an amplitude of a first temporal portion of the electrical signal according to a level of the measured condition, wherein a second temporal portion of the feedback signal represents a reference voltage level, wherein the first temporal portion and the second temporal portion are non-overlapping in time, and wherein the reference voltage level corresponds to a voltage across a diode of the implantable device;
outputting, by the implantable device and to the external device, the feedback signal; and
delivering, by the implantable device, a level of electrical stimulation therapy proportional to the level of the electrical power transduced from the energy signal such that the implantable device delivers a reduced level of the electrical stimulation therapy where the level of the electrical power is reduced.

35. The method of claim 34, wherein the measured condition of the patient includes one or more of a pH level, a glucose level, an oxygen level, a temperature level, and a pressure level.

36. A method comprising:
outputting, by an external device, an energy signal to be transduced into electrical power by an implantable device that delivers a level of electrical stimulation therapy proportional to a level of the electrical power transduced from the energy signal, wherein the implantable device does not include either a stimulation generator or a power source;
receiving, by the external device and from the implantable device, a feedback signal that includes a truncation point in a first temporal portion that represents a level of a condition of a patient in which the implantable device is implanted, wherein the level of the condition is measured by a sensor included in the implantable device, wherein a second temporal portion of the feedback signal represents a reference voltage level, wherein the first temporal portion and the second temporal portion are non-overlapping in time, and wherein the reference voltage level corresponds to a voltage across a diode of the implantable device; and
determining, by the external device and based on the feedback signal, the level of the measured condition.

37. The method of claim 36, wherein the feedback signal further represents an absolute level of the electrical power transduced from the energy signal, and wherein the first temporal portion of feedback signal further includes:
a first parameter that represents a level of the electrical power transduced from the energy signal, the method further comprising:
adjusting, by the external device and based on the determined absolute level of the electrical power, a level of the energy signal to control the level of electrical stimulation therapy delivered by the implantable device; and
outputting, by the external device, the energy signal with the adjusted level.

38. The method of claim 37, wherein the measured condition of the patient includes one or more of a pH level, a glucose level, an oxygen level, a temperature level, and a pressure level.

* * * * *